United States Patent
Shuman

(10) Patent No.: US 6,827,086 B2
(45) Date of Patent: Dec. 7, 2004

(54) DEVICE AND METHOD OF ISOLATING DELETERIOUS BODY TISSUE LOCATED WITHIN HEALTHY BODY TISSUE

(75) Inventor: Brandon James Shuman, Kirkland, WA (US)

(73) Assignee: Spiration, Inc., Redmond, WA (US)

( * ) Notice: Subject to any disclaimer, the term of this patent is extended or adjusted under 35 U.S.C. 154(b) by 262 days.

(21) Appl. No.: 10/061,755

(22) Filed: Feb. 1, 2002

(65) Prior Publication Data

US 2003/0149446 A1 Aug. 7, 2003

(51) Int. Cl.[7] .............................................. A61B 19/00
(52) U.S. Cl. ...................................... 128/898; 606/205
(58) Field of Search ................................ 606/107, 110, 606/111, 205, 207, 210, 211

(56) References Cited

U.S. PATENT DOCUMENTS

| | | | |
|---|---|---|---|
| 4,402,445 A | * 9/1983 | Green | 227/19 |
| 4,888,015 A | * 12/1989 | Domino | 623/6.12 |
| 5,147,369 A | 9/1992 | Wagner | |
| 5,207,702 A | * 5/1993 | Pearl | 606/207 |
| 5,366,475 A | 11/1994 | Voss et al. | |
| 5,693,069 A | * 12/1997 | Shallman | 606/205 |

* cited by examiner

Primary Examiner—Julian W. Woo
Assistant Examiner—Charles H. Sam
(74) Attorney, Agent, or Firm—Knobbe, Martens, Olson & Bear, LLP

(57) ABSTRACT

The invention provides for treating deleterious body tissue located within healthy body tissue by isolating the deleterious tissue from blood, air, and fluid communication. The device includes two structures, each having a corresponding circumferential surface arranged to circumscribe the deleterious body tissue. When the first and second circumferential surfaces are brought together in an aligned relationship with the deleterious body tissue between the structures, the two circumferential surfaces co-act to isolate the deleterious body tissue from communication with the healthy body tissue. The deleterious tissue is resected according to the invention by allowing it to become ischemic and necrotic, or by excision.

4 Claims, 6 Drawing Sheets

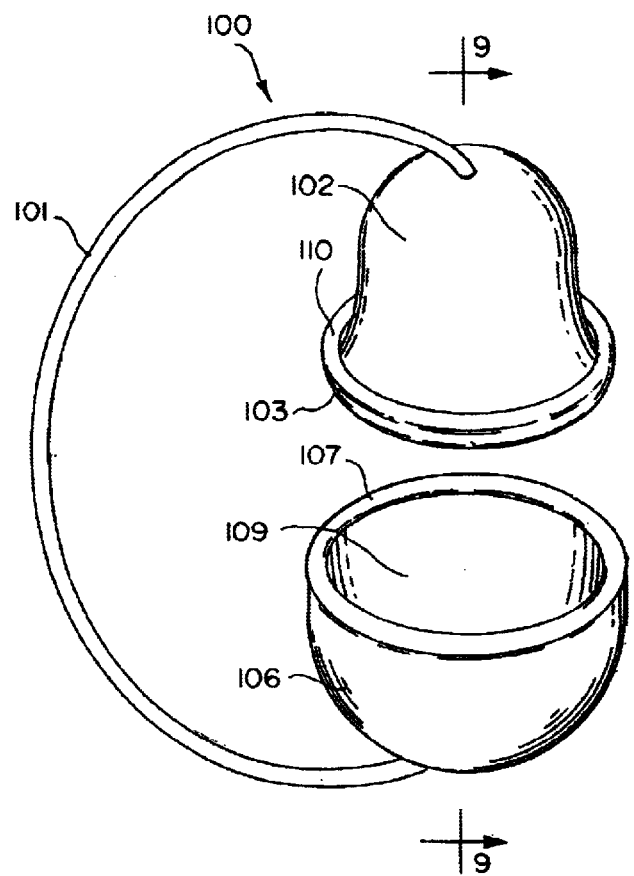
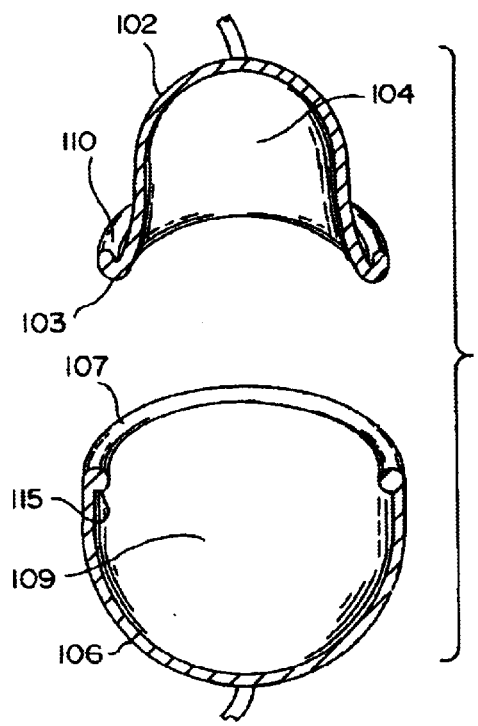

DEVICE AND METHOD OF ISOLATING DELETERIOUS BODY TISSUE LOCATED WITHIN HEALTHY BODY TISSUE

BACKGROUND OF THE INVENTION

The present invention is generally directed to a device for and method of treating deleterious body tissue located within healthy body tissue by isolating the deleterious body tissue from fluid, air, and blood communication. Once isolated, the deleterious body tissue may be resected by allowing it to become ischemic and necrotic, or excised.

Cancer is a form of deleterious body tissue. Pulmonary cancer is the leading cause of cancer deaths in the United States. Early detection and proper treatment of cancerous tissue significantly improves survival rates. Asymptomatic, spherical, intrapulmonary lesions are found in about 1 of every 500 chest films. Solitary lesions having a diameter of 3 cm or less are presently defined as pulmonary nodules. Larger lesions are defined as masses. Currently, a pulmonary nodule proves to be a malignant tumor in about 40% of the cases, most often bronchogenic carcinoma but occasionally a solitary metastasis or carcinoid tumor.

A number of different procedures, techniques, and apparatus are available to treat pulmonary nodules, each having morbidity and mortality considerations that must be evaluated along with the operable risk to the patient. Any procedure involving the lungs is invasive and fraught with potential complications, including bleeding and lung air leaks. Lung tissue is very thin and fragile, and hence difficult to suture together without bleeding and air leaks. After a lung is resectioned, current procedures and techniques often restructure the remaining lung portion with suture staples.

Current techniques and related apparatus do not adequately address the potential complications caused by resectioning pulmonary tissue, particularly bleeding and air leaks. When bleeding and air leaks occur, a more invasive procedure is often indicated with possible increased morbidity and mortality. In addition, current techniques and related apparatus often unnecessarily require removal of a significant amount of lung tissue to resection a nodule, and are not as effective when a nodule is located away from an edge.

In view of the foregoing, there in a need in the art for a new and improved apparatus and method of treating pulmonary nodules that minimizes potential complications and risks of other procedures, including removal of excessive tissue, air leaks, and bleeding. The present invention is directed to such an improved apparatus and method.

SUMMARY OF THE INVENTION

The present invention provides a device for treating deleterious body tissue located within healthy body tissue. The device isolates deleterious body tissue from the healthy tissue by limiting blood, air, and fluid communication with the deleterious body tissue. The device includes a first structure having a first circumferential surface arranged to circumscribe the deleterious body tissue. The device also includes a second structure having a second circumferential surface corresponding to the first circumferential surface. When the first and second circumferential surfaces are brought together in an aligned relationship with the deleterious body tissue between the first and second structures, the first and second circumferential surfaces co-act to isolate the deleterious body tissue from communication with the healthy body tissue. When the first and second circumferential surfaces of the device are together in an aligned relationship, the first structure and the second structure may define a chamber arranged to contain the deleterious body tissue.

In another version of the invention, the device may include a bias element coupled to the first structure and the second structure. The bias element brings the circumferential surfaces of the first and second structures together in an aligned relationship. The bias element may further include bringing the first and second circumferential surfaces together with sufficient force that the deleterious body tissue becomes ischemic and necrotic. The first and second structures may each further include a first and second aperture respectively, so that when the circumferential surfaces are brought together in an aligned relationship, the first aperture and second aperture expose the deleterious body tissue for resection.

In a further version of the invention, the device includes the capability to excise the deleterious body tissue. The circumferential surface of at least one of the first and second structures of the device includes a cutting edge that resects deleterious body tissue when the first and second circumferential surfaces are brought together in an aligned relationship. One of the first and second structures of the device may also include a cutting surface arranged to engage at least a portion of the cutting edge on the other one of the first and second structures when the first and second circumferential surfaces are brought together in an aligned relationship. Bringing the cutting edge against the cutting surface resects the deleterious body tissue. The device may further include a bias element coupled to the first structure and the second structure. The bias element brings the circumferential surfaces of the first and second structures together in an aligned relationship with sufficient force such that the deleterious body tissue enclosed therein is resected.

In yet another version of the invention, the device may include interlocking surfaces to maintain the co-action of the circumferential surfaces to isolate the deleterious body tissue. The first structure includes a first interlocking surface, and the second structure includes a second interlocking surface. The interlocking surfaces are arranged to interlock with the deleterious body tissue between. Upon bringing the first and second circumferential surfaces together to a point of interlocking, the circumferential surfaces of the first and second structures will compress tissue surrounding a perimeter of the deleterious body tissue enclosed therein with sufficient force such that the deleterious body tissue will be isolated from communication with the healthy body tissue, and become ischemic and necrotic. The interlocking surfaces may be urged together by an external force. The first structure and the second structure may define a chamber arranged to contain at least the pulmonary nodule when the interlocking surfaces are interlocked. Further, the device may include a bias element coupled to the first structure and the second structure that brings the first structure and second structure together in the aligned relationship.

In another version of the invention, a device is provided that includes two structures that move together in a shearing manner and that compress the deleterious body tissue between to limit blood, air, and fluid communication. The device includes a first structure having a first partial circumferential surface, and a second structure having a second partial circumferential surface corresponding to the first circumferential surface. The first and second partial circumferential surfaces are arranged to encircle the deleterious body tissue when the first structure and the second structure are brought toward each other in a shearing manner with the deleterious body tissue encircled between the first and second partial circumferential surfaces. When brought together in this manner, the first and second circumferential surfaces co-act to isolate the deleterious body tissue from communicating with the healthy body tissue. The device may include a bias element coupled to the first structure and the second structure. The bias element brings the circumferential surfaces of the first and second structures toward each other in the shearing manner with sufficient force such that deleterious body tissue enclosed therein becomes ischemic and necrotic.

In still another version of the invention, a method is provided for isolating deleterious body tissue located within healthy body tissue from the healthy body tissue by limiting blood, air, and fluid communication with the deleterious body tissue. The method includes several steps. One step includes providing a device having a first structure that includes a first circumferential surface arranged to circumscribe the deleterious body tissue, and a second structure that includes a second circumferential surface corresponding to the first circumferential surface. Another step includes placing the deleterious body tissue to be isolated between the first circumferential surface and the second circumferential surface of the device. A further step includes bringing the first and second circumferential surfaces of the device together in an aligned relationship with the deleterious body tissue between the first and second structures. The first and second circumferential surfaces co-act to isolate the deleterious body tissue from communication with the healthy body tissue. The method may include the further step of bringing the first circumferential surface and the second circumferential surface together against the healthy body tissue immediately surrounding the deleterious body tissue with sufficient force that the deleterious body tissue becomes ischemic and necrotic. The device of the method may include a bias element coupled to the first structure and the second structure that brings the circumferential surfaces of the first and second structures together. The first and second structures of the device may include a first and second aperture arranged so that when the circumferential surfaces are brought together in the aligned relationship, the first aperture and second aperture expose the deleterious body tissue for excision. The exposed deleterious body tissue may then be resected.

In yet still another version of the invention, a device is provided for isolating deleterious body tissue located within healthy body tissue from the healthy body tissue by limiting blood, air, and fluid communication with the deleterious body tissue. The device includes a confining means having at least two circumferential surfaces, the circumferential surfaces being arranged in combination to circumscribe the deleterious body tissue and to be brought together in an aligned, co-acting relationship to isolate the deleterious body tissue. The device may include a means arranged for maintaining the circumferential surfaces together with sufficient force that deleterious body tissue confined therein will be isolated from communication with healthy body tissue.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

FIG. 8 is a perspective view of yet another pulmonary nodule isolation device embodying the invention;

FIG. 9 illustrates a cross-sectional view of the pulmonary nodule isolation device illustrated in FIG. 8;

DETAILED DESCRIPTION OF THE PREFERRED EMBODIMENTS

Briefly stated, the invention treats deleterious body tissue within healthy body tissue by bringing two circumferential surfaces together and compressing the deleterious body tissue between them. The compression isolates the deleterious tissue from blood and fluid communication with surrounding healthy body tissue. The deleterious tissue is resected by allowing it to become ischemic and necrotic due to its isolation, or by excision.

Figure 1:
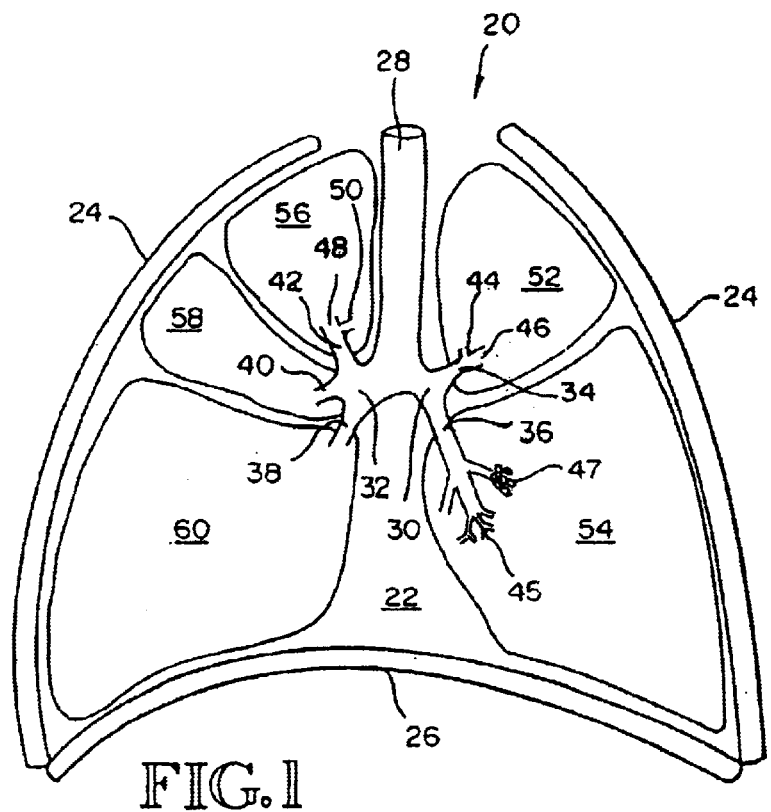
FIG. 1 is a simplified sectional view of a thorax illustrating a healthy respiratory system.

FIG. 1 is a sectional view of a healthy respiratory system. The respiratory system 20 resides within the thorax 22, which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. The sub-branches end in terminal bronchioles 45, and alveoli clusters 47.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes and alveoli to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
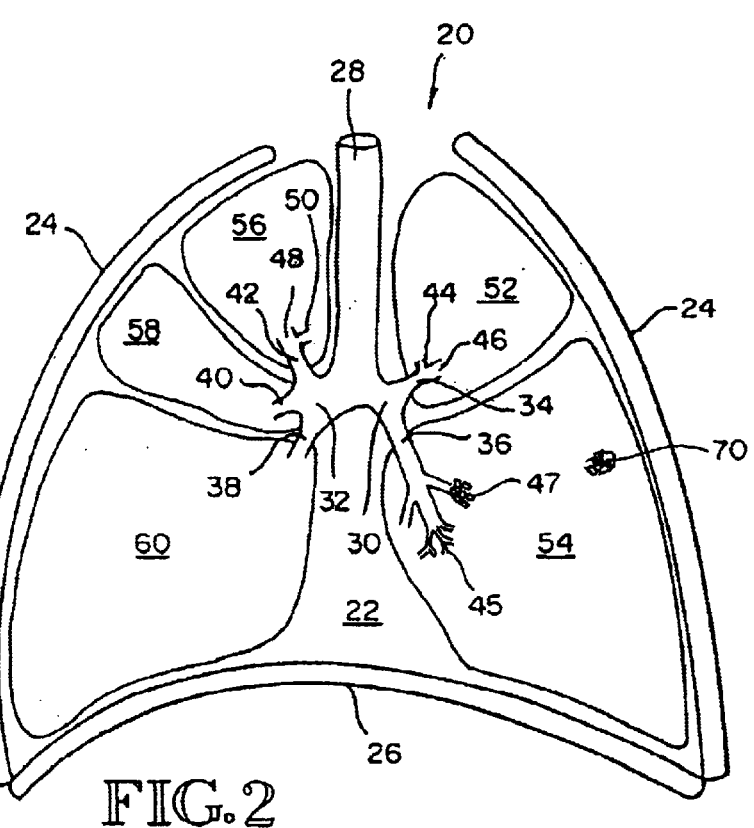
FIG. 2 illustrates a solitary pulmonary nodule in a lung.

FIG. 2 illustrates a pulmonary nodule in a lung. The invention is illustrated using a pulmonary nodule as an instance of deleterious body tissue. However, the invention is not limited to treating pulmonary nodules.

While pulmonary nodule 70 is illustrated in left lung lobe 54, pulmonary nodules may be located in any portion and in any structure of a lung. Pulmonary nodules are defined in current practice as lesions having a diameter of approximately 3 cm or less. They may have any contour (smooth, lobulated, or speculated) and may or may not be calcified. Larger lesions are called masses. Pulmonary nodules receive blood and fluid communication from surrounding healthy body tissue.

Figure 3:
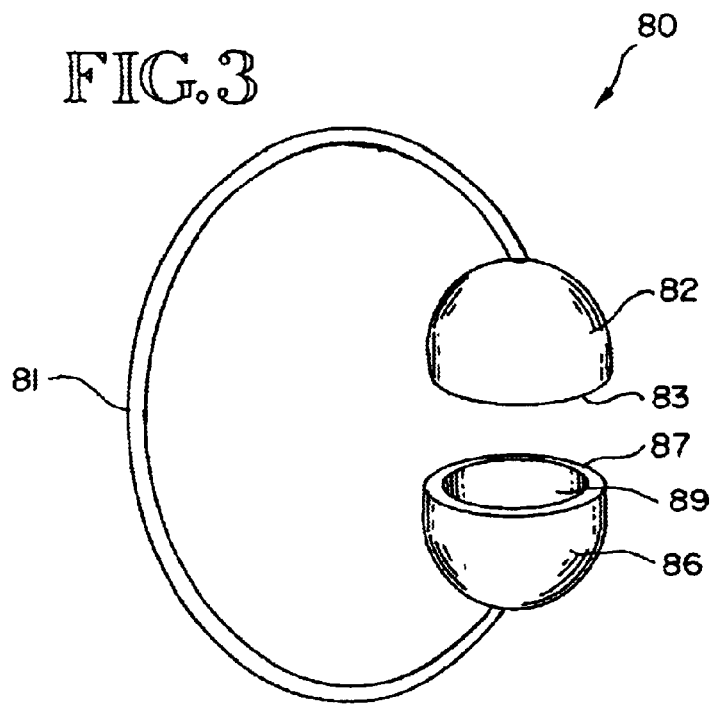
FIG. 3 is a view of a pulmonary nodule isolation device embodying the present invention.

FIG. 3 is a view of a pulmonary nodule isolation device embodying the present invention. Pulmonary nodule isolation device 80 includes bias element 81, first structure 82, first circumferential surface 83, first structure chamber 84 (not shown), second structure 86, second circumferential surface 87, and second structure chamber 89.

Figure 7:
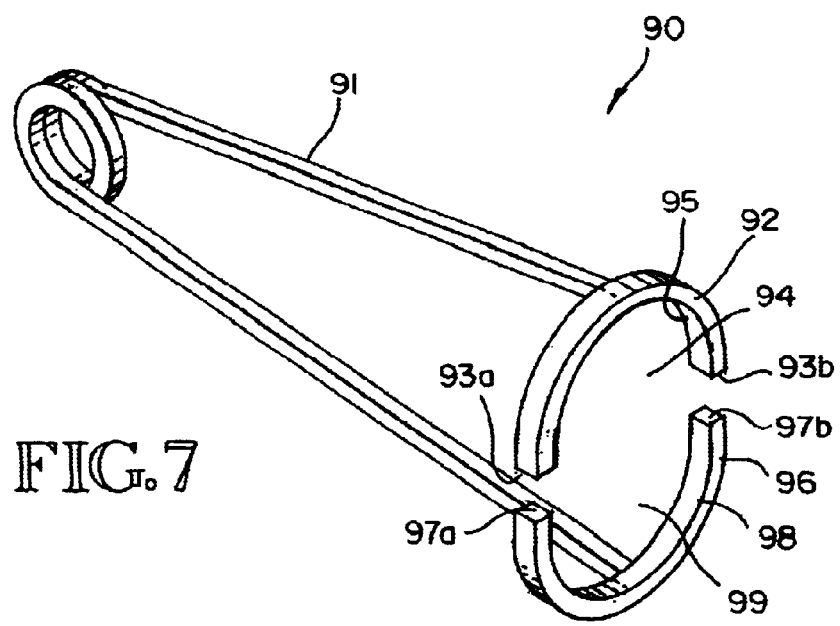
FIG. 7 is a perspective view of another pulmonary nodule isolation device embodying the invention.

First structure 82 and second structure 86 may be made from any material suitable for use in a human body that is capable of transmitting compressive force to healthy body tissue surrounding a pulmonary node, as described in additional detail below. First circumferential surface 83 and second circumferential surface 87 may be any shape and width suitable for enclosing pulmonary nodule 70 and applying pressure to the surrounding tissue. Their shape is generally circular in this embodiment. While FIG. 3 illustrates first and second structures 82 and 86 as being hemispherically shaped, the structures may be ring-shaped as illustrated in FIGS. 7 and 8. Bias element 81 is coupled to the first structure 82 and the second structure 86, and brings first structure circumferential surface 83 and second structure circumferential surface 87 together in aligned relationship. In this preferred embodiment, bias element 81 employs spring characteristics of a metal to bring the surfaces together and exert a compressive force. The operation of pulmonary nodule isolation device 80 is described in conjunction with FIGS. 4–6.

The first circumferential surface 83 and the second circumferential surface 87 do not need to be in a single plane. In this and all other embodiments, they may be any configuration that, when placed in alignment, will isolate a pulmonary nodule from fluid and blood communication with surrounding healthy body tissue.

Figure 4:
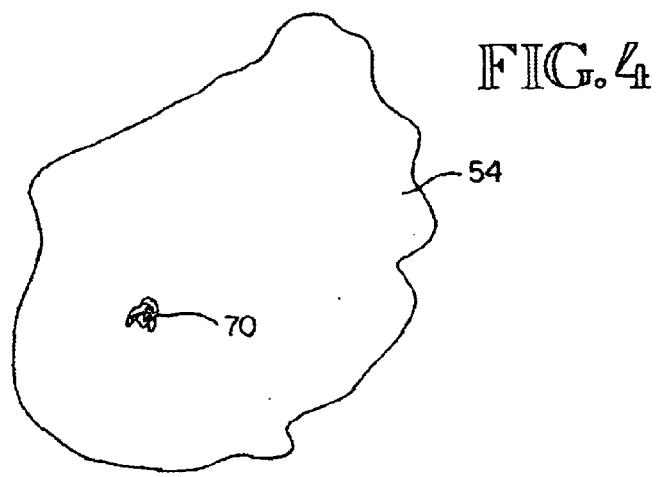
FIG. 4 illustrates a portion of a left lung lobe with a pulmonary nodule to be isolated.
Figure 5:
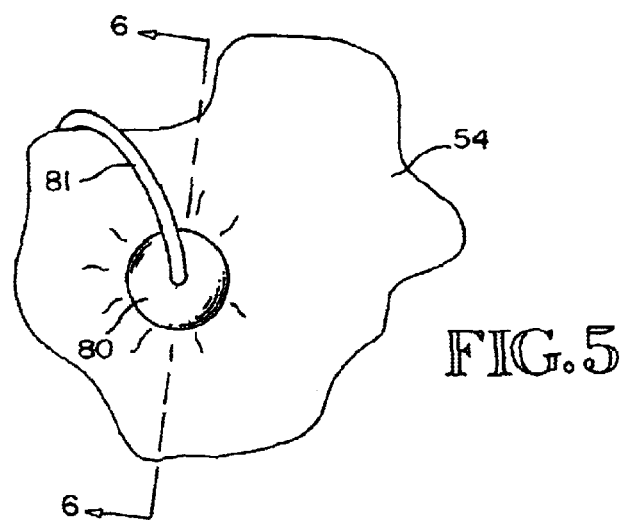
FIG. 5 illustrates one structure of a pulmonary nodule isolation device enclosing tissue immediately surrounding the pulmonary nodule and being brought in aligned relationship by a bias element.
Figure 6:
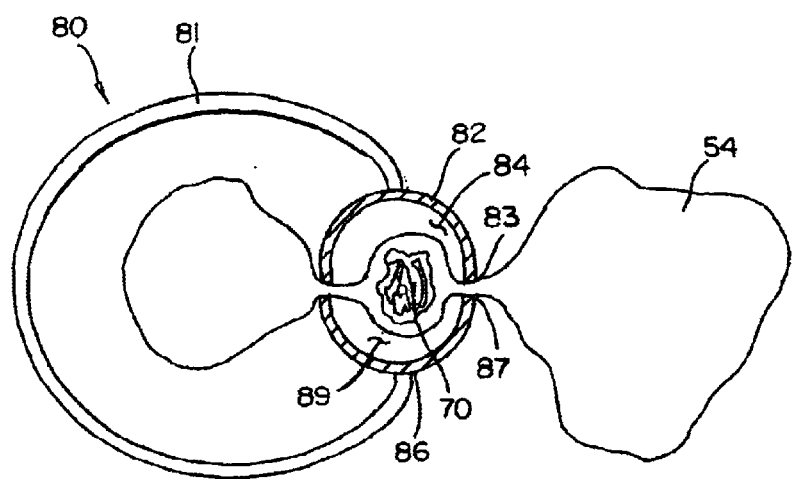
FIG. 6 illustrates a cross-sectional view of a first structure and a second structure enclosing a pulmonary nodule.

FIGS. 4–6 are views illustrating pulmonary nodule isolation device 80 isolating and resecting a portion of a lung containing a pulmonary nodule according to an embodiment of the present invention. FIG. 4 illustrates a portion of left lung lobe 54 with pulmonary nodule 70 to be isolated.

In operation, the pulmonary nodule for treatment is located in a lung. Device 80 may be used in the middle of a lung as well as on an edge. An appropriately sized pulmonary nodule isolation device 80 is selected that will engage a predetermined amount of healthy lung tissue surrounding nodule 70. This will spare other lung tissue by removing only a very small amount of tissue. The selected pulmonary nodule isolation device 80 is readied for resection. The first structure 82 and the second structure 86 are separated against the force of bias element 81. The first circumferential surface 83 and the second circumferential surface 87 are placed over nodule 70 and healthy body tissue immediately surrounding it. Bias element 81 then is allowed to bring the first circumferential surface 83 and the second circumferential surface 87 together in an aligned relationship and compress the healthy body tissue immediately surrounding the perimeter of pulmonary nodule 70.

FIG. 5 illustrates one structure of pulmonary nodule isolation device 80 enclosing healthy body tissue immediately surrounding pulmonary nodule 70 (which is obscured by the device) and being brought in aligned relationship by bias element 81. The pulmonary nodule 70 is enclosed and compressed thereby.

FIG. 6 illustrates a cross-sectional view of first structure 82 and second structure 86 enclosing pulmonary nodule 70 and a portion of lung tissue surrounding pulmonary nodule 70. The cross-sectional view looks into an edge of a plane formed by the first circumferential surface 83 and the second circumferential surface 87. The first circumferential surface 83 and the second circumferential surface 87 are in aligned relationship, and the bias element 81 compresses the surfaces against lung tissue surrounding pulmonary nodule 70. The compression isolates pulmonary node 70 from air, blood and fluid communication (hereafter collectively referred to as "communication") with the surrounding healthy body tissue and the remainder of left lung 54. The isolation from blood and fluid communication causes pulmonary nodule 70 to become ischemic and necrotic. The isolation from air communication minimizes the chance of air leaks when pulmonary nodule 70 becomes ischemic and necrotic, or is excised.

The first structure chamber 84 and the second structure chamber 89 may be configured to retain a necrotized pulmonary nodule. Device 80 is arranged to be fast and easy to place on the lung tissue surrounding pulmonary nodule 70. Its use significantly reduces the possibility of bleeding and air leaks.

FIG. 7 is a view of another pulmonary nodule isolation device embodying the invention. Pulmonary nodule isolation device 90 includes bias element 91, first structure 92 having a first interior circumferential surface 95, first structure stops 93a and 93b, first structure enclosure 94, second structure 96 having a second interior circumferential surface 98, second structure stops 97a and 97b, and second structure enclosure 99.

The elements of pulmonary nodule isolation device 90 are made and arranged in a manner similar to spherical pulmonary nodule isolation device 80.

The first structure 92 and the second structure 96 are horseshoe or elliptically shaped, lie in a plane, arranged to enclose a pulmonary nodule and its surrounding tissue, and apply pressure by movement in a shearing manner. The first structure 92 and the second structure 96 may be configured to form any shape suitable for enclosing a perimeter of a pulmonary nodule. Bias element 91 couples first structure 92 and second structure 96. Bias element 91 provides a movable compressive force bringing first structure stops 93 and second structure stops 97 in an aligned relationship. The first stops 93a and 93b, and the second stops 97a and 97b, may be any configuration to limit the movement of first structure 92 in the direction of second structure 96, and thus define a minimum area enclosed (the combined areas of first structure enclosure 94 and second structure enclosure 99). In this preferred embodiment, bias element 91 employs spring characteristics of a metal to bring the structures together in an aligned relationship and to exert a compressive force. In an alternative embodiment, first structure 92 and second structure 96 may be arranged to move past each other in a shearing manner without the range of shearing movement being limited by first stops 93a and 93b, and second stops 97a and 97b.

The operation of pulmonary isolation device 90 is substantially similar to spherical pulmonary nodule isolation device 80. First structure 92 and second structure 96 are separated against the force of bias element 91. The first structure circumferential inner surface 94 and the second structure circumferential inner surface 98 are placed over nodule 70 and tissue immediately surrounding it. Bias element 91 urges the first structure circumferential inner surface 95 and the second structure circumferential inner surface 98 toward each other in a shearing manner. The first stops 93a and 93b, and the second stops 97a and 97b are available to limit the range of movement. The tissue immediately surrounding the perimeter of the pulmonary nodule is enclosed and compressed thereby, and is isolated from communication with surrounding healthy body tissue, including blood, air, and fluid. The nodule 70 will then become ischemic and necrotic.

FIGS. 8 and 9 are views of yet another pulmonary nodule isolation device embodying the invention. FIG. 8 is a perspective view of pulmonary nodule isolation device 100. FIG. 9 illustrates a cross-sectional view of pulmonary nodule isolation device 100 from approximately the same perspective illustrated in FIG. 8, the cross-section taken through approximately the vertical midline. Pulmonary nodule isolation device 100 includes retaining member 101, first structure 102, first circumferential surface 103, first structure chamber 104, first structure interlocking surface 110, second structure 106, second circumferential surface 107, second structure chamber 109, and second structure interlocking surface 115.

The elements of pulmonary nodule isolation device 100 are made and arranged in a manner similar to spherical pulmonary nodule isolation device 80 as described in conjunction with FIG. 3. The first structure 102 and the second structure 106 are arranged so that one structure interlocks with the other in any manner known to one having ordinary skill in the art, including overlapping and by fitting together of projections and recesses. In an alternative embodiment illustrated in FIGS. 8 and 9, the first structure 102 interlocks into the second structure 106 by the projection of the first interlocking surface 110 into a recess formed by the second structure interlocking surface 115. First interlocking surface 110 and second interlocking surface 115 are arranged to interlock the two structures together, and to provide sufficient compressive force when interlocked so that a pulmonary nodule enclosed in device 100 will be isolated from communication with surrounding tissue, and become ischemic and necrotic. Linking member 101 maintains the first structure 102 and the second structure 106 in general proximity with each other, but is not required to provide orientation or compressive bias.

Pulmonary nodule isolation device 100 operates in a manner similar to spherical pulmonary nodule isolation device 80 described in conjunction with FIGS. 3 and 4. First structure 102 and second structure 106 are placed over healthy body tissue immediately surrounding a perimeter of pulmonary nodule 70 to be resectioned, and moved into opposition by an external force to a point where the first structure interlocking surface 110 and the second structure interlocking surface 115 interlock. Bringing the first structure 102 and the second structure 106 to a point of interlocking compresses tissue surrounding a perimeter of pulmonary nodule 70. Compressive force on the tissue surrounding a perimeter of pulmonary nodule 70 is maintained during interlock, such that pulmonary nodule 70 enclosed in device 100 will be isolated from communication with surrounding healthy body tissue, and become ischemic and necrotic.

Figure 10:
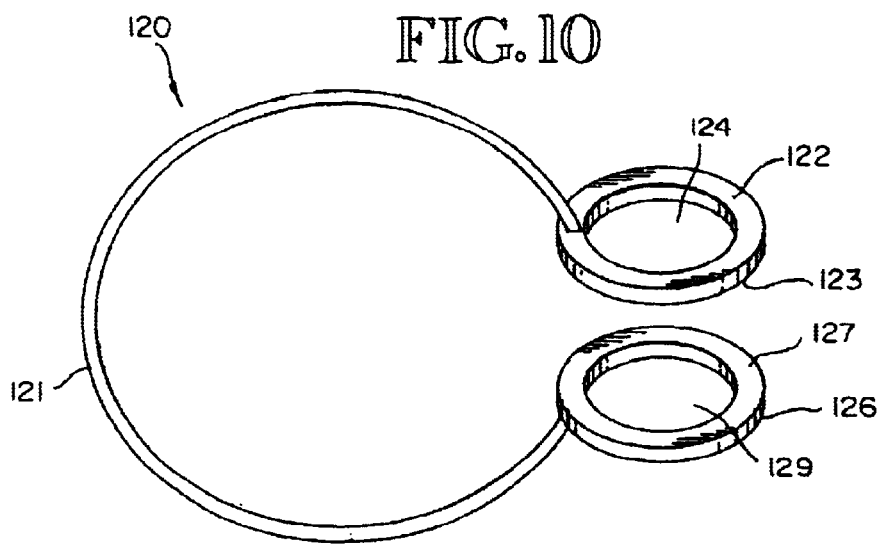
FIG. 10 is a perspective view of a further pulmonary nodule isolation device embodying the invention.
Figure 11:
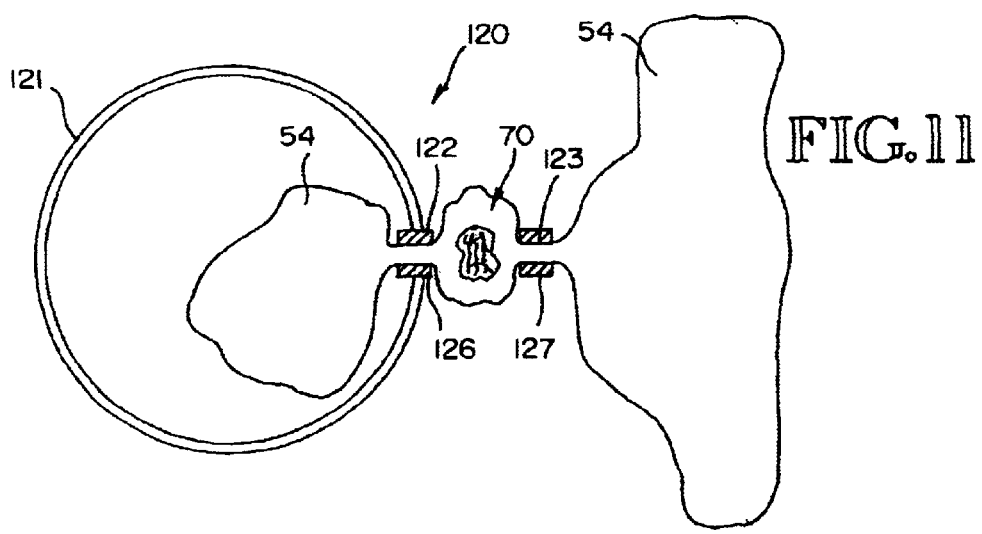
FIG. 11 illustrates a cross-sectional view of a portion of a left lung lobe with a pulmonary nodule to be resectioned employing the pulmonary nodule isolation device illustrated in FIG. 10.
Figure 12:
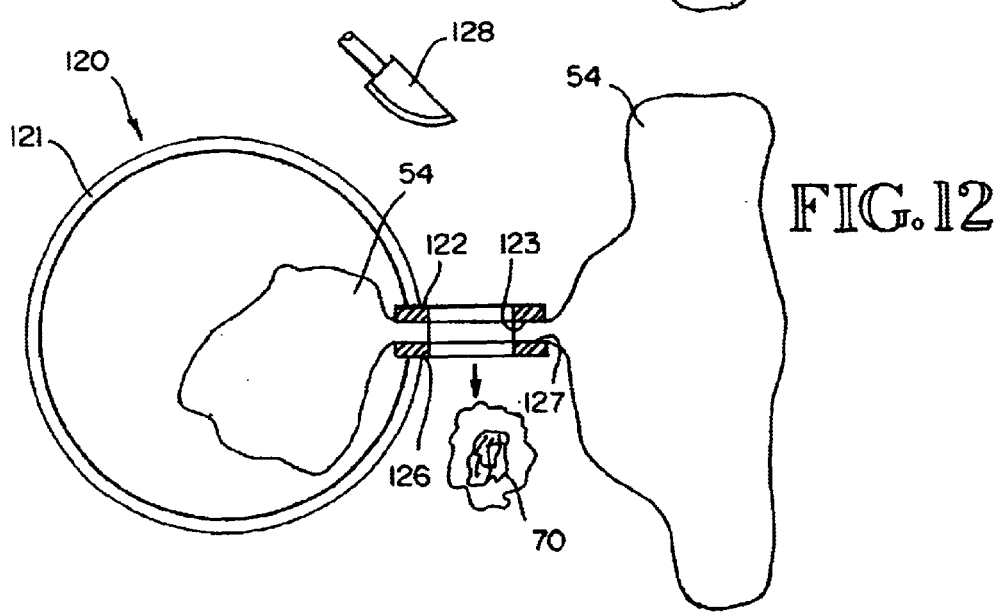
FIG. 12 illustrates a cross-section view similar to FIG. 11 where the pulmonary nodule has been excised from a lung by a scalpel.

FIGS. 10–12 are views of a further pulmonary nodule isolation device and method embodying the invention. FIG. 10 is a perspective view of pulmonary nodule isolation device 120, which includes bias element 121, first structure 122, first circumferential surface 123, first structure aperture 124, second structure 126, second circumferential surface 127, and second structure aperture 129.

The elements of the pulmonary nodule isolation device 120 are made and arranged in a manner similar to pulmonary nodule isolation device 80 disclosed in conjunction with FIG. 3. In an alternative embodiment, structures 122 and 126 are generally ring-shaped. When the circumferential surfaces (123, 127) of the first and second structures are in opposition, the first structure aperture 124 and the second structure aperture 129 are in approximate alignment and will expose at least the pulmonary nodule 70.

FIGS. 11 and 12 illustrate a method of using the pulmonary nodule isolation device 120 to resection a portion of lung 54. FIG. 11 illustrates a cross-sectional view of a portion of left lung lobe 54 with pulmonary nodule 70 to be resectioned. The cross-sectional view looks into an edge of the plane formed by the first circumferential surface 123 and the second circumferential surface 127 when they are in an aligned relationship. Pulmonary nodule 70 may be on an edge or in the middle of lung 54. A pulmonary nodule isolation device 120 is selected having the first structure aperture 124 and the second structure aperture 129 sized to expose only a predetermined amount of healthy body tissue surrounding pulmonary nodule 70. FIG. 7b further illustrates bias element 121 locating and bringing the first structure 122 and the second structure 126 in an aligned relationship, and compressing them against lung tissue surrounding a perimeter of pulmonary nodule 70. The pulmonary nodule 70 and its surrounding tissue are positioned within first aperture structure 124 and second aperture structure 129, and exposed. Nodule 70 may then be excised.

FIG. 12 illustrates a cross-section view similar to FIG. 11 where pulmonary nodule 70 has been excised from lung 54 by scalpel 128. In accordance with this embodiment, the lung 54 may be resectioned by removing only a very small amount of healthy body tissue around the circumference of pulmonary nodule 70, with reduced probability of air leaks and bleeding.

Figure 13:
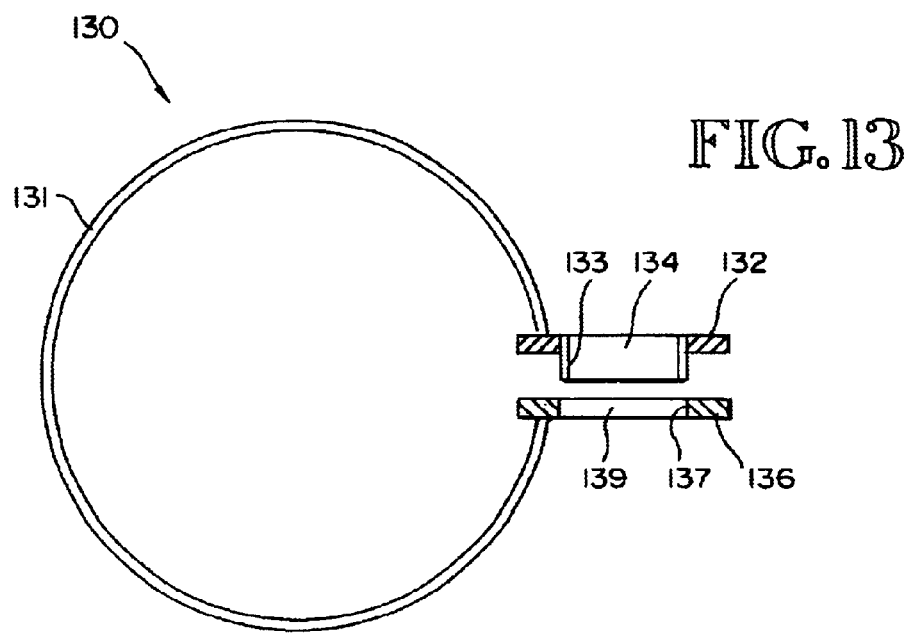
FIG. 13 is a cross-sectional view illustrating another pulmonary nodule isolation device that includes a circumferential blade to resection a pulmonary nodule according to the invention.
Figure 14:
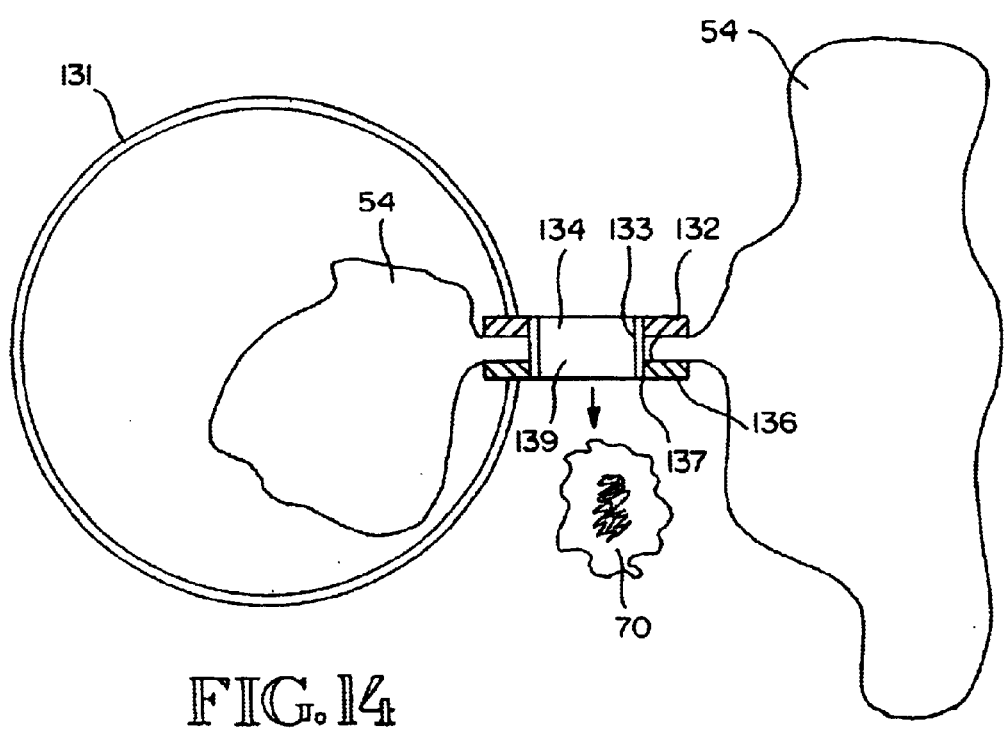
FIG. 14 illustrates using pulmonary nodule isolation device illustrated in FIG. 13 to resect a portion of a lung.

FIGS. 13 and 14 are views of another pulmonary nodule isolation device and method embodying the invention. FIG. 13 is a cross-sectional view illustrating the pulmonary nodule isolation device 130 according to an embodiment of the invention. The cross-sectional view looks into an edge of the plane formed by the first circumferential surface 133 and the second circumferential surface 137 when they are in an aligned relationship. Pulmonary nodule isolation device 130 is configured similarly to pulmonary nodule isolation device 120 described in FIG. 10, with blade 133 being added to excise nodule 70. Pulmonary nodule isolation device 130 includes a bias element 131, a first ring 132, a blade 133, a first ring aperture 134, a second ring 136, a second ring cutting surface 137, and a second ring aperture 139.

The elements of pulmonary nodule isolation device 130 are made and arranged in a manner similar to the pulmonary nodule isolation device 80 disclosed in conjunction with FIG. 3. Rings 132 and 136 are generally circular, but may be any shape suitable for enclosing the periphery of pulmonary nodule 70, including elliptical and rectangular. Blade 133 forms a circumferential cutting edge that is included in at least one of first ring 132 and second ring 136, and may be any material usable in the human body sufficiently sharp to excise pulmonary nodule 70. In an alternative embodiment, a portion of blade 133 may be included in first ring 132 and another portion in second ring 136, the portions combining to form a circumferential cutting edge. Second ring cutting surface 137 forms a circumferential surface that is arranged to engage blade 133 to excise pulmonary node 70 in response to the first ring 132 and the second ring 136 being brought into an aligned relationship. When first ring 132 and second ring 136 are brought into an aligned relationship, first aperture 134 and second aperture 139 are also in approximate alignment, blade 133 and second ring cutting surface 137 are in approximate cutting alignment, and pulmonary node 70 is encircled therein.

FIG. 14 illustrates using pulmonary nodule isolation device 130 to resection a portion of lung 54. The method is initially similar to that described in conjunction with FIGS. 11 and 12. FIG. 14 illustrates, in a cross-section view, resectioning a portion of left lung lobe 54. FIG. 14 illustrates the same cross-sectional view as FIG. 13. Pulmonary nodule 70 and a predetermined amount of surrounding healthy body tissue are positioned within first ring aperture 134 and second ring aperture 139. This places the blade 133 and the second ring cutting surface 137 in approximate cutting alignment. Bias element 81 brings first ring 132 against second ring 136, in an aligned relationship with force. This force causes the blade 133 and the second ring cutting surface 137 to engage and excise the lung tissue surrounding pulmonary nodule 70. In accordance with this embodiment, the lung 54 may again be resectioned by removing only a very small amount of good tissue around the circumference of pulmonary nodule 70, with reduced probability of air leaks and bleeding.

As can thus be seen from the foregoing, the present invention provides a new and improved device and method of treating pulmonary nodules that minimizes removal of excessive lung tissue, air leaks, and bleeding. This is achieved by an device that compresses tissue around the periphery of a pulmonary nodule or other tissue, isolating it from blood and fluid communication and causing it to become ischemic and necrotic, or allowing it to be excised.

While particular embodiments of the present invention have been shown and described, modifications may be made, and it is therefore intended in the appended claims to cover all such changes and modifications which fall within the true spirit and scope of the invention.

What is claimed is:

1. A method of isolating deleterious body tissue located within healthy body tissue from the healthy body tissue by limiting blood and fluid communication with the deleterious body tissue, the method comprising the steps of:

providing a device comprising:
a first structure, including a first circumferential surface arranged to circumscribe the deleterious body tissue; and
a second structure, including a second circumferential surface corresponding to the first circumferential surface;

placing the deleterious body tissue to be isolated between the first circumferential surface and the second circumferential surface of the device; and bringing the first and second circumferential surfaces of the device together in an aligned relationship with the deleterious body tissue between the first and second structures, wherein the first and second circumferential surfaces co-act to isolate the deleterious body tissue from communication with the healthy body tissue without severing the deleterious body tissue from the healthy body tissue.

2. The method of claim 1, further including the step of bringing the first circumferential surface and the second circumferential surface together against the healthy body tissue immediately surrounding the deleterious body tissue with sufficient force that the deleterious body tissue becomes ischemic and necrotic.

3. The method of claim 2, wherein the device further comprises a bias element coupled to the first structure and the second structure that brings the circumferential surfaces of the first and second structures together.

4. The method of claim 1, wherein the first and second structures of the device further respectively comprise a first and second aperture arranged so that when the circumferential surfaces are brought together in the aligned relationship, the first aperture and second aperture expose the deleterious body tissue for resection, and wherein the method includes the further step of resecting the deleterious body tissue.

* * * * *